US012740709B2

(12) United States Patent
Li et al.

(10) Patent No.: US 12,740,709 B2
(45) Date of Patent: Sep. 22, 2026

(54) WEARABLE MODULE

(71) Applicant: ROCKLEY PHOTONICS LIMITED, Altrincham (GB)

(72) Inventors: Shuhe Li, Pasadena, CA (US); David McCann, Pasadena, CA (US)

(73) Assignee: Rockley Photonics Limited, Altrincham (GB)

(*) Notice: Subject to any disclaimer, the term of this patent is extended or adjusted under 35 U.S.C. 154(b) by 337 days.

(21) Appl. No.: 18/454,706

(22) Filed: Aug. 23, 2023

(65) Prior Publication Data

US 2024/0065553 A1 Feb. 29, 2024

Related U.S. Application Data

(60) Provisional application No. 63/400,713, filed on Aug. 24, 2022.

(51) Int. Cl.
*A61B 5/00* (2006.01)

(52) U.S. Cl.
CPC .......... *A61B 5/0075* (2013.01); *A61B 5/6801* (2013.01)

(58) Field of Classification Search
CPC . A61B 5/0075; A61B 5/6801; A61B 5/14552; A61B 5/0004; A61B 5/002; A61B 5/0022; A61B 5/02416; A61B 5/02427; A61B 5/4806; A61B 5/6832; A61B 5/68335; A61B 5/02438; A61B 5/6814; A61B 5/6822; A61B 5/6824; A61B 5/6826; A61B 5/7435; A61B 5/746; A61B 2560/0285; A61B 2562/0295; A61B 2562/166; A61B 2562/185; A61B 5/6813; G01J 3/0205; G01J 3/0256; G01J 3/0262; G01J 3/0291; G01J 3/42; G01J 3/021;
(Continued)

(56) References Cited

U.S. PATENT DOCUMENTS 3,965,735 A * 6/1976 Hartung ............... G01B 11/272 73/862.55
5,567,972 A * 10/1996 Abe ........................ H10F 77/50 257/E31.118

(Continued)

FOREIGN PATENT DOCUMENTS

JP 2015129257 A * 7/2015 ........... H10H 20/857
WO WO 2021/130749 A1 7/2021
WO WO 2022/064273 A1 3/2022

OTHER PUBLICATIONS

International Search Report and Written Opinion of the International Searching Authority, Mailed Jan. 23, 2024, Corresponding to PCT/IB2023/000517, 12 pages.

*Primary Examiner* — Pascal M Bui Pho
*Assistant Examiner* — Nicholas A Robinson
(74) *Attorney, Agent, or Firm* — Womble Bond Dickinson (US) LLP

(57) ABSTRACT

A wearable device. In some embodiments, a system includes a wearable device configured to be worn against the skin of a subject, including: a transmitting window; a light source for generating light for transmission through the transmitting window; a receiving window; a photodetector configured to detect light received through the receiving window; and an opaque barrier, an edge of the transmitting window being separated from an edge of the receiving window by a gap having a width of less than 2 mm, and the opaque barrier being in the gap.

8 Claims, 17 Drawing Sheets

(58) Field of Classification Search
CPC ........ G01J 3/027; G01J 3/10; G01J 2003/104; G16H 40/67; G01D 11/245; H04N 23/51; H05K 5/00
See application file for complete search history.

(56) References Cited

U.S. PATENT DOCUMENTS

| | | | | |
|---|---|---|---|---|
| 5,584,296 | A * | 12/1996 | Cui | A61B 5/14553 356/41 |
| 2005/0023573 | A1 * | 2/2005 | Govil | G02B 26/0825 359/224.1 |
| 2008/0221410 | A1 * | 9/2008 | Campbell | G01N 21/474 600/323 |
| 2013/0280923 | A1 * | 10/2013 | Sade | B23K 26/0661 438/795 |
| 2020/0330012 | A1 * | 10/2020 | Lamego | A61B 5/002 |
| 2020/0340860 | A1 * | 10/2020 | Fish | G01J 3/0259 |
| 2022/0082670 | A1 * | 3/2022 | Chou | G01S 7/4861 |
| 2022/0354389 | A1 * | 11/2022 | Ben Ishay | A61B 5/681 |

* cited by examiner

WEARABLE MODULE

CROSS-REFERENCE TO RELATED APPLICATION(S)

The present application claims priority to and the benefit of U.S. Provisional Application No. 63/400,713, filed Aug. 24, 2022, entitled "OPTICAL INTERFACE WITH DEFORMABLE MIRROR", the entire content of which is incorporated herein by reference.

FIELD

One or more aspects of embodiments according to the present disclosure relate to spectrophotometry, and more particularly to a wearable module including a spectrophotometer.

BACKGROUND

Spectrophotometry may be an effective technique for obtaining information about the composition of a sample, such as the tissues of the skin, and below the skin, of a subject.

It is with respect to this general technical environment that aspects of the present disclosure are related.

SUMMARY

According to an embodiment of the present disclosure, there is provided a system, including: a wearable device configured to be worn against the skin of a subject, including: a transmitting window; a light source for generating light for transmission through the transmitting window; a receiving window; a photodetector configured to detect light received through the receiving window; and an opaque barrier, an edge of the transmitting window being separated from an edge of the receiving window by a gap having a width of less than 2 mm, and the opaque barrier being in the gap.

In some embodiments, the opaque barrier is opaque to light at a wavelength in the range from 2000 nm to 2500 nm.

In some embodiments, the receiving window is parallel, to within 5 degrees, to the transmitting window.

In some embodiments, the receiving window is coplanar, at the gap, to within 0.5 mm, with the transmitting window.

In some embodiments, the receiving window is cylindrical and has a cylindrical outer surface.

In some embodiments, the transmitting window has a circular hole, having a larger diameter than the receiving window.

In some embodiments, the opaque barrier has a cylindrical outer surface fitting against the inner surface of the circular hole, and a bore having a cylindrical inner surface fitting against the cylindrical surface of the receiving window.

In some embodiments, the cylindrical inner surface is offset from the cylindrical outer surface.

In some embodiments, at a thinnest point, the opaque barrier has a thickness of less than 1 mm.

In some embodiments, at the thinnest point, the opaque barrier has a thickness of less than 0.5 mm.

In some embodiments, the system includes a photodetector enclosure including the receiving window and the opaque barrier, wherein: the photodetector enclosure includes a step at an end of the bore, and a lower surface of the receiving window abuts against the step.

In some embodiments: the photodetector enclosure further includes a flange, and a lower surface of the transmitting window abuts against an upper surface of the flange.

In some embodiments, the system includes: a package base including the light source, and a lid, the lid including: the transmitting window, the receiving window, and a photodetector.

In some embodiments, a lower surface of the lid abuts against an upper surface of a flange of the package base, and a gap between the lid and the package base enables the lid to slide, on the upper surface of the flange, in a direction parallel to the upper surface of the flange.

In some embodiments, the lid includes a threaded hole for receiving a threaded part, the threaded part being configured, when turned, to cause the lid to slide on the upper surface of the flange.

In some embodiments, the system further includes a reflector for reflecting light from the light source through the transmitting window.

In some embodiments, the reflector is a deformable reflector.

In some embodiments, the system includes a piezoelectric actuator configured, when driven by an electric drive signal, to cause the deformable reflector to deform.

In some embodiments, the light source includes: a photonic integrated circuit, including a waveguide having an output facet at an edge of the photonic integrated circuit; and a lens, secured to the edge of the photonic integrated circuit.

In some embodiments, the wearable device is waterproof.

BRIEF DESCRIPTION OF THE DRAWINGS

These and other features and advantages of the present disclosure will be appreciated and understood with reference to the specification, claims, and appended drawings wherein:

Each of the drawings is drawn to scale, for a respective embodiment.

DETAILED DESCRIPTION

The detailed description set forth below in connection with the appended drawings is intended as a description of exemplary embodiments of a wearable module including a spectrophotometer provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

Figure 1A:
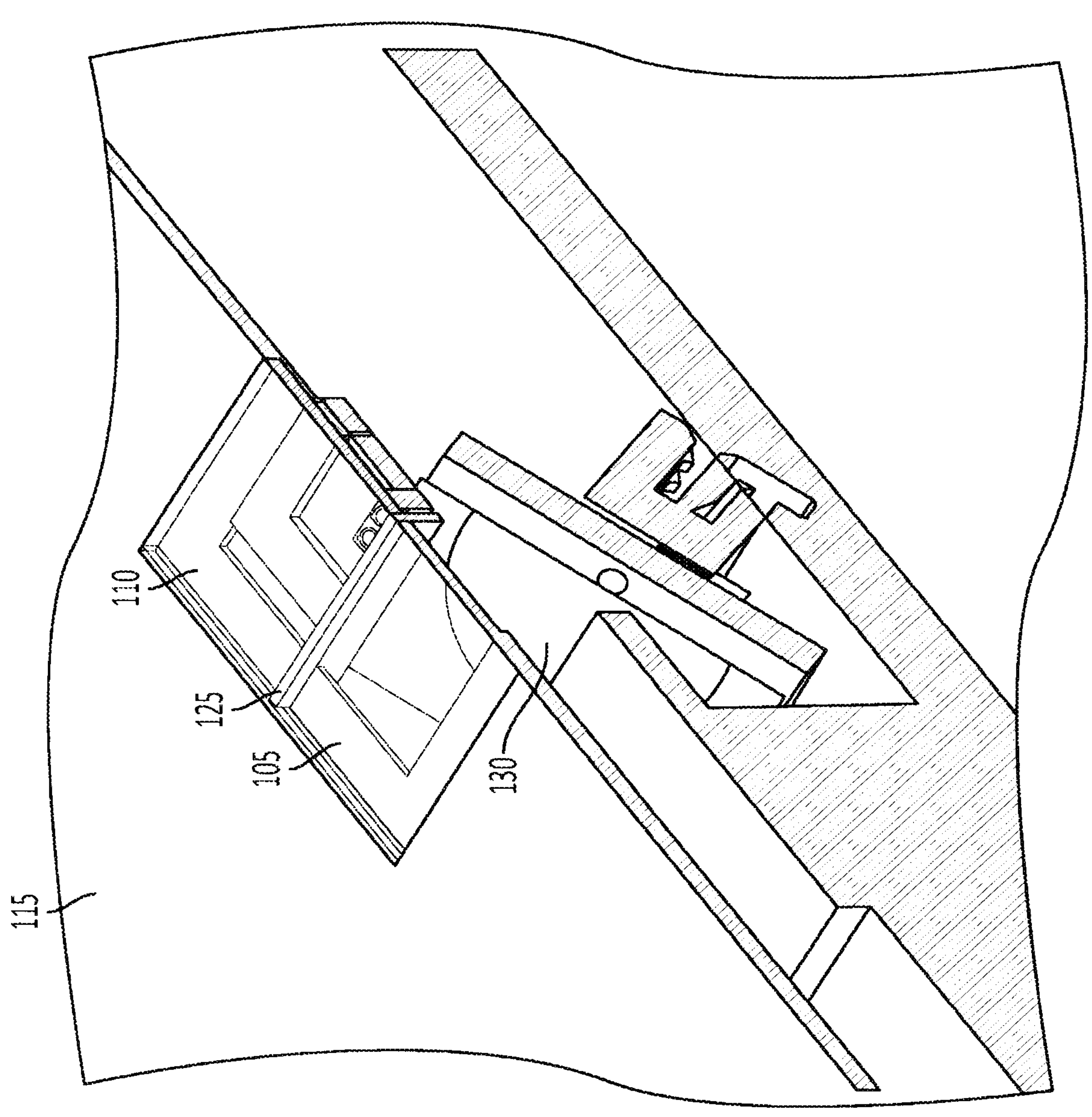
FIG. 1A is a perspective cutaway view of a portion of a wearable module including a spectrophotometer, according to an embodiment of the present disclosure.

Referring to FIG. 1, in some embodiments, a spectrophotometer module 100 (FIGS. 4A and 4B) includes a light source (not visible in FIG. 1), the light from which is used as a probe beam transmitted through a transmitting window 105 and into a sample (e.g., the skin of a subject (e.g., a patient)). After interacting with the sample (e.g., tissues of the patient) a portion of the probe beam may return to the module, into which the portion may be transmitted through a receiving window 110, and within which it may be detected by a photodetector 112 (PD) such as a photodiode (FIG. 2G). Each of the transmitting window 105 and the receiving window 110 may be set into a surface (which may be referred to as the "skin contact surface") 115 of the module, which in operation may be pressed against the skin of the subject, e.g., the module may be a wearable device secured by a strap 120 (FIGS. 4A and 4B) to the head or torso of the subject or to a limb of the subject, with the skin contact surface 115 of the module abutting against the skin of the subject.

The fraction of the probe beam that returns to the photodetector 112, after interacting with (e.g., scattering from) the sample, may be relatively small; as such, it may be advantageous to avoid the transmission of light from the light source to the photodetector 112 via any path that does not include a portion within the sample. This may be accomplished by enclosing the photodetector 112 in an optically sealed compartment. This compartment may include an opaque barrier 125 between the transmitting window 105 and the receiving window 110, to prevent light from the light source from propagating (i) inside the transmitting window 105 (e.g., in a direction substantially parallel to the skin contact surface 115) to the edge of the transmitting window 105, (ii) from the edge of the transmitting window 105 into a nearby edge of the receiving window 110, and then (iii) to the photodetector 112. In some embodiments, the gap between the transmitting window 105 and the receiving window 110 is made to be small (e.g., between 0.05 mm and 2 mm, or less than 0.3 mm) so that the minimum length through the sample of an optical path extending through the transmitting window 105 and through the receiving window 110 may be relatively short. The transmitting window 105 and the receiving window 110 may be parallel to within 5 degrees, and coplanar to within 0.5 mm at the gap between the transmitting window 105 and the receiving window 110.

Figure 2A:
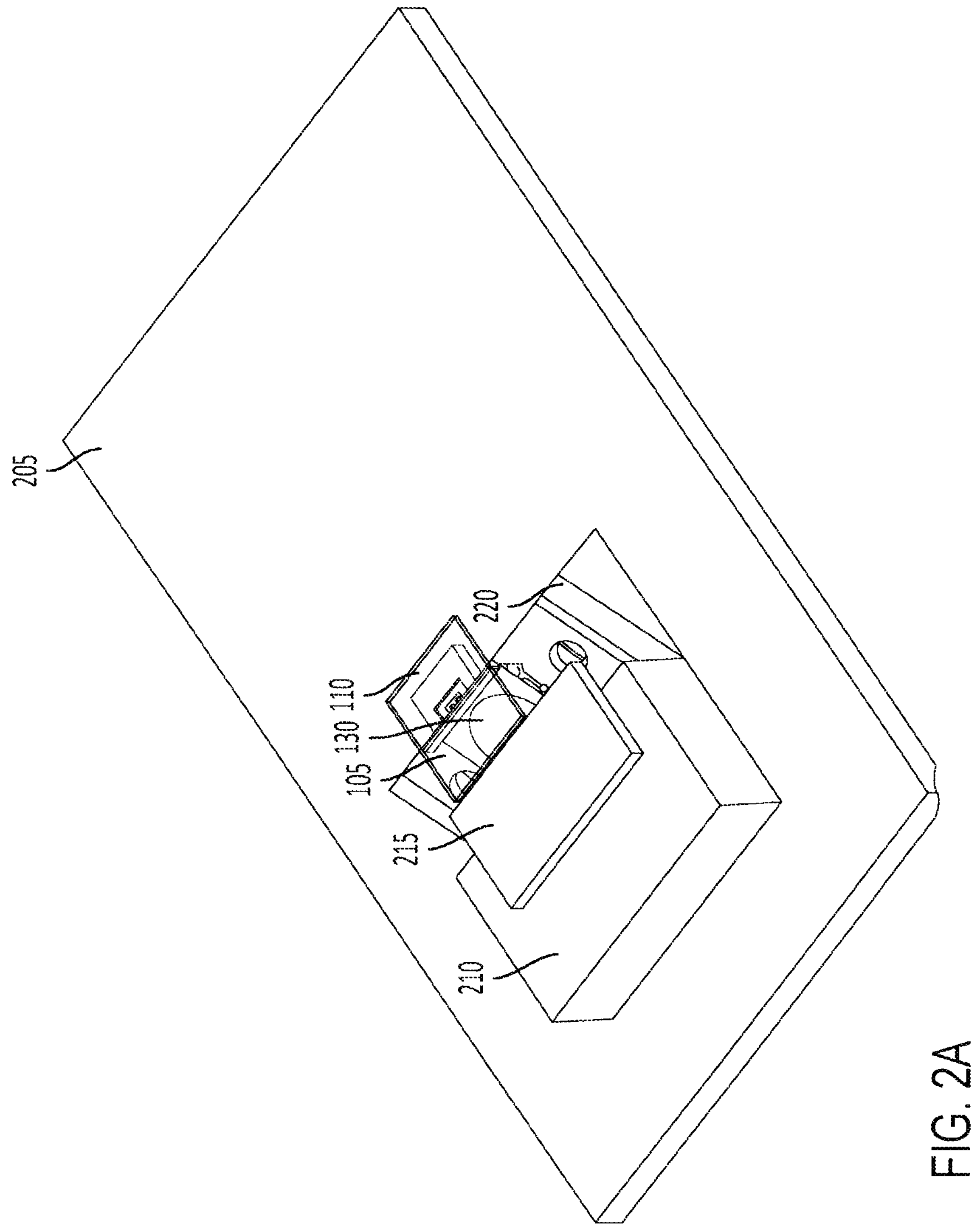
FIG. 2A is a perspective view of a portion of a wearable module, according to an embodiment of the present disclosure.
Figure 2B:
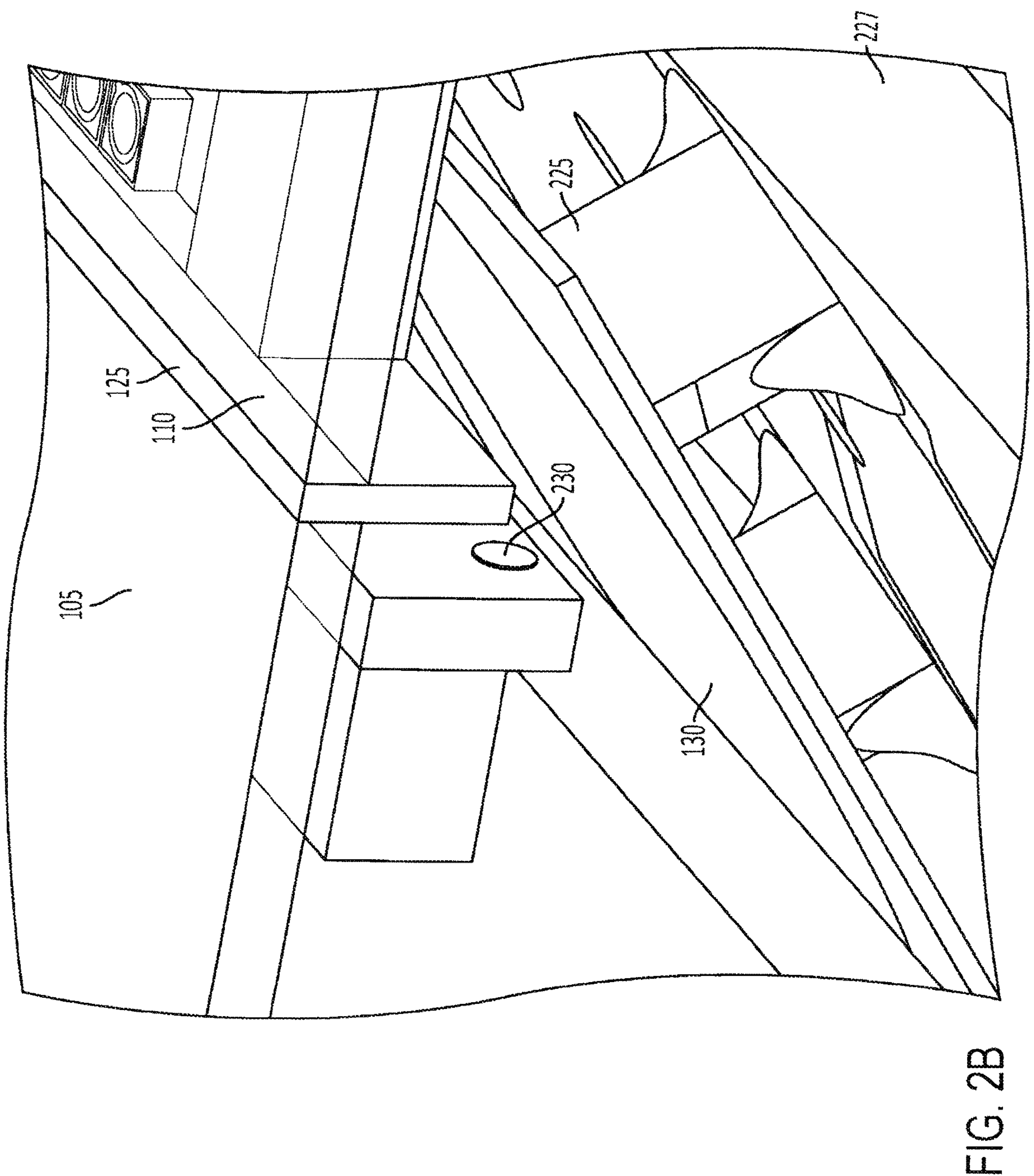
FIG. 2B is a perspective view of a portion of a wearable module, according to an embodiment of the present disclosure.
Figure 2C:
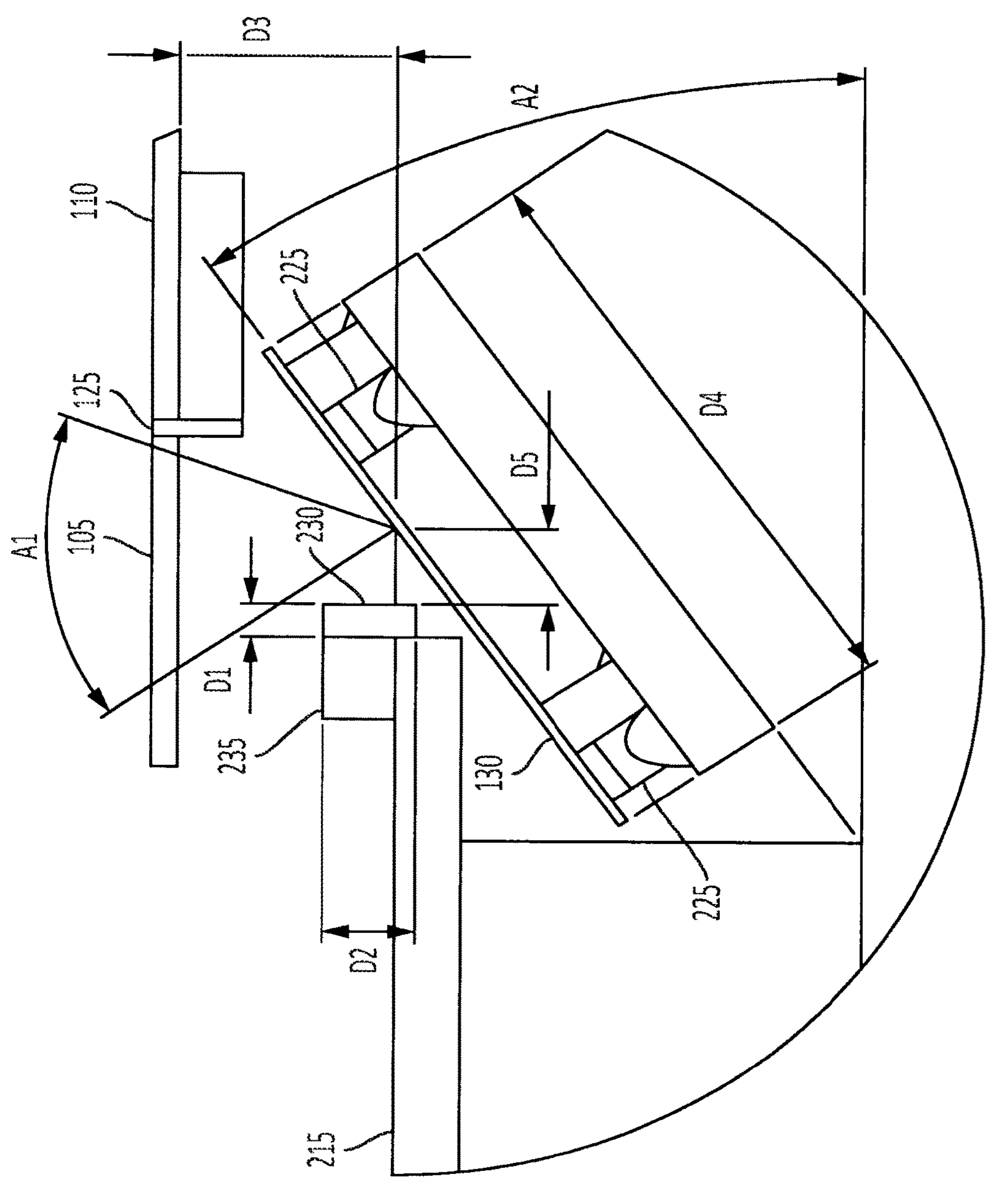
FIG. 2C is a side view of a portion of a wearable module, according to an embodiment of the present disclosure.

The light source may emit coherent (e.g., laser) light, and it may emit light in a direction substantially parallel to the skin contact surface 115; the light may be reflected to propagate through the transmitting window 105 in a direction that is perpendicular, or nearly perpendicular, to the skin contact surface 115 (see, e.g., FIG. 2C). The reflector used for this purpose may be a deformable mirror reflector (DMR) 130, the surface of which may be deformable and driven, in operation, so that its shape changes with time, so as to modify the coherence properties of the light transmitted through the transmitting window 105 in a manner that reduces speckle noise at the photodetector 112.

Figure 1B:
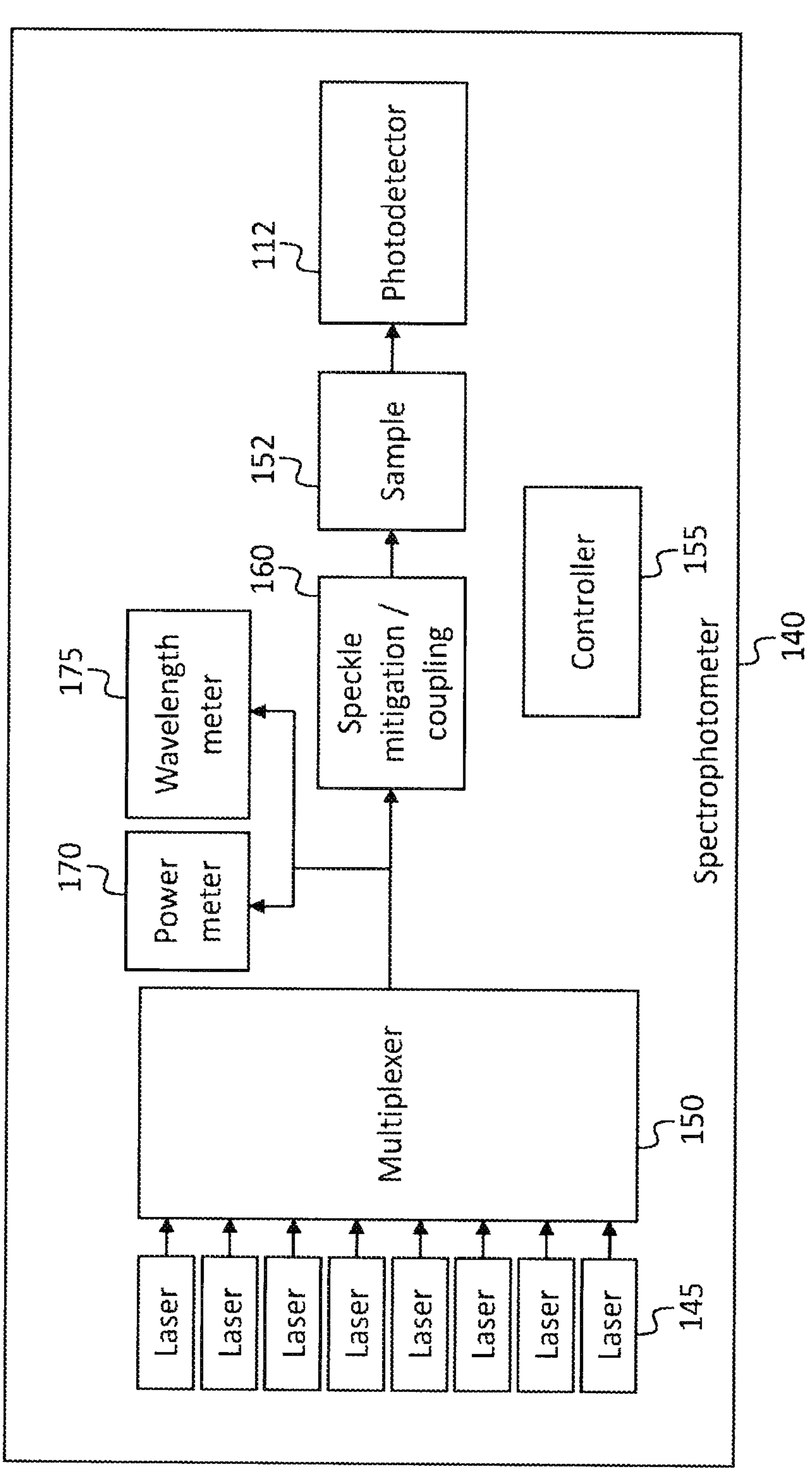
FIG. 1B is a block diagram of a spectrophotometer, according to an embodiment of the present disclosure.

FIG. 1B is a block diagram of a spectrophotometer 140, in some embodiments. Each laser 145 of an array of lasers 145 (e.g., ten or more lasers 145, not all of which are shown) is connected to a wavelength multiplexer 150 (which may be, e.g., an arrayed waveguide grating, an echelle grating, or a cascade of Mach-Zehnder interferometers). Each laser 145 may include an InP reflective semiconductor optical amplifier (RSOA) coupled to a waveguide on a silicon photonic integrated circuit (a silicon PIC). The waveguide on the silicon photonic integrated circuit may include a grating reflector that sets the operating wavelength of the laser. Each laser 145 operates at a different respective wavelength and is connected to an input, corresponding to the operating wavelength of the laser, of the wavelength multiplexer 150. In operation, one laser is turned on at a time (e.g., by a controller 155, which may be or include a processing circuit), so that the combination of (i) the array of lasers 145 and (ii) the wavelength multiplexer 150 operates as a swept wavelength light source. In other embodiments, a different swept wavelength light source (e.g., a single widely tunable laser, or a source including an array of tunable lasers, each tunable over a different wavelength range) is used instead of the array of lasers 145 and the wavelength multiplexer 150 shown in FIG. 1B. In the embodiment of FIG. 1B, the wavelength separation between lasers 145 that are adjacent in wavelength may be between 5 nm and 50 nm, and the wavelength range may be about 2000 nm to 2500 nm (e.g., 2080 nm to 2400 nm). In some embodiments, one or more gaps may be present in the set of wavelengths (e.g., if a wavelength band within the range is of limited use because of strong absorption by water in the band).

Figure 3C:
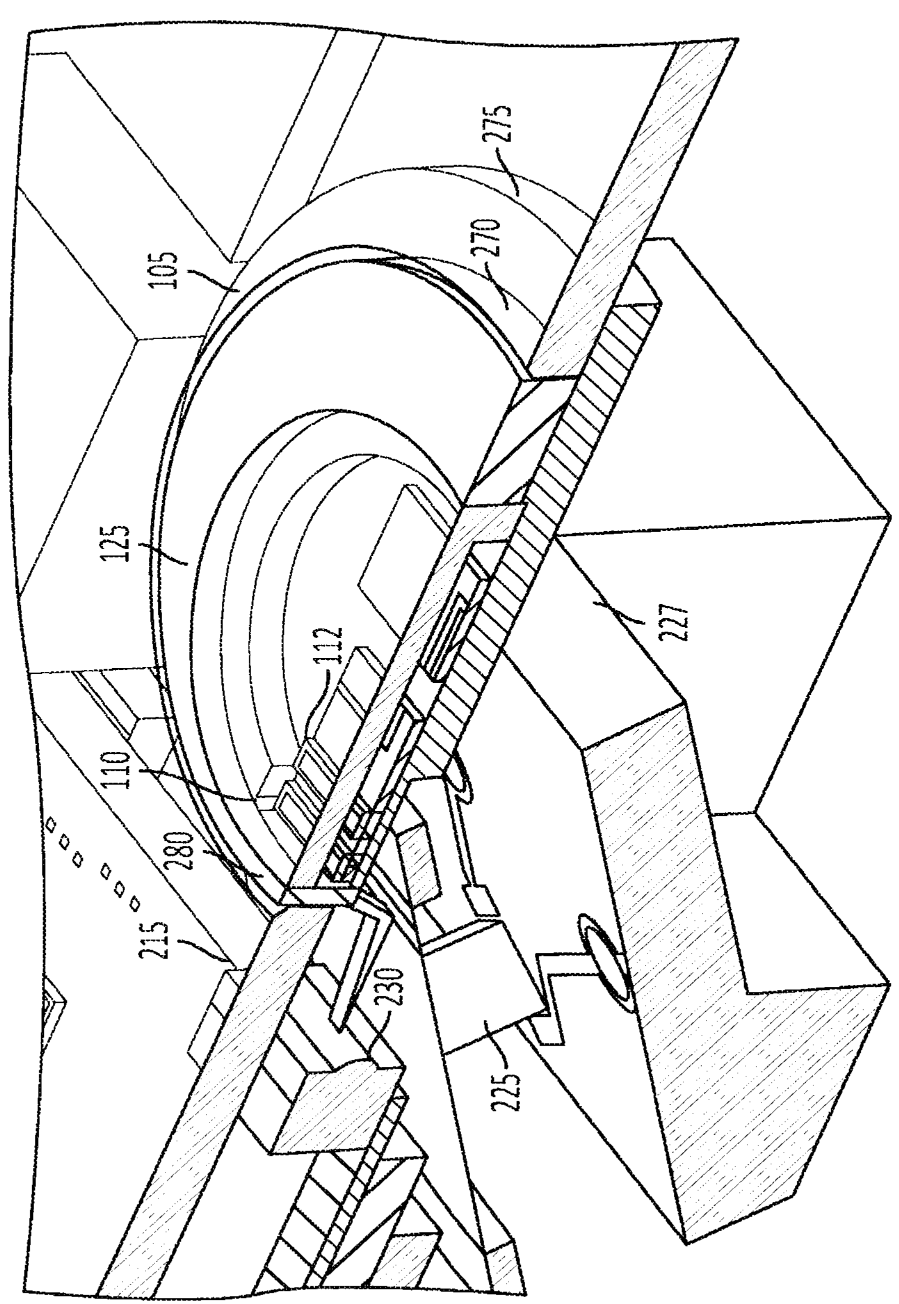
FIG. 3C is a perspective cutaway view of a portion of a wearable module, according to an embodiment of the present disclosure.
Figure 4A:
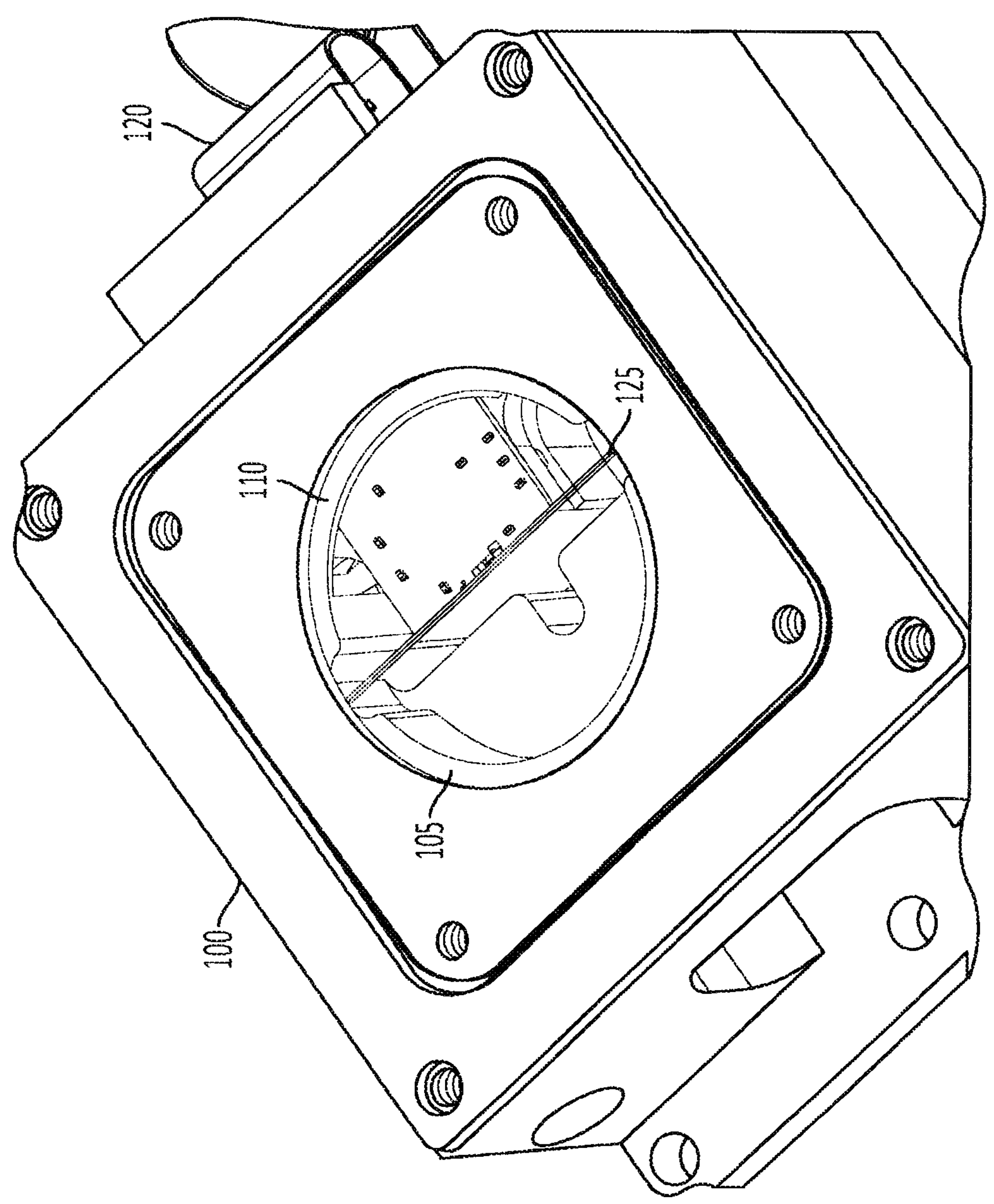
FIG. 4A is a perspective view of a portion of a wearable module, according to an embodiment of the present disclosure.
Figure 4B:
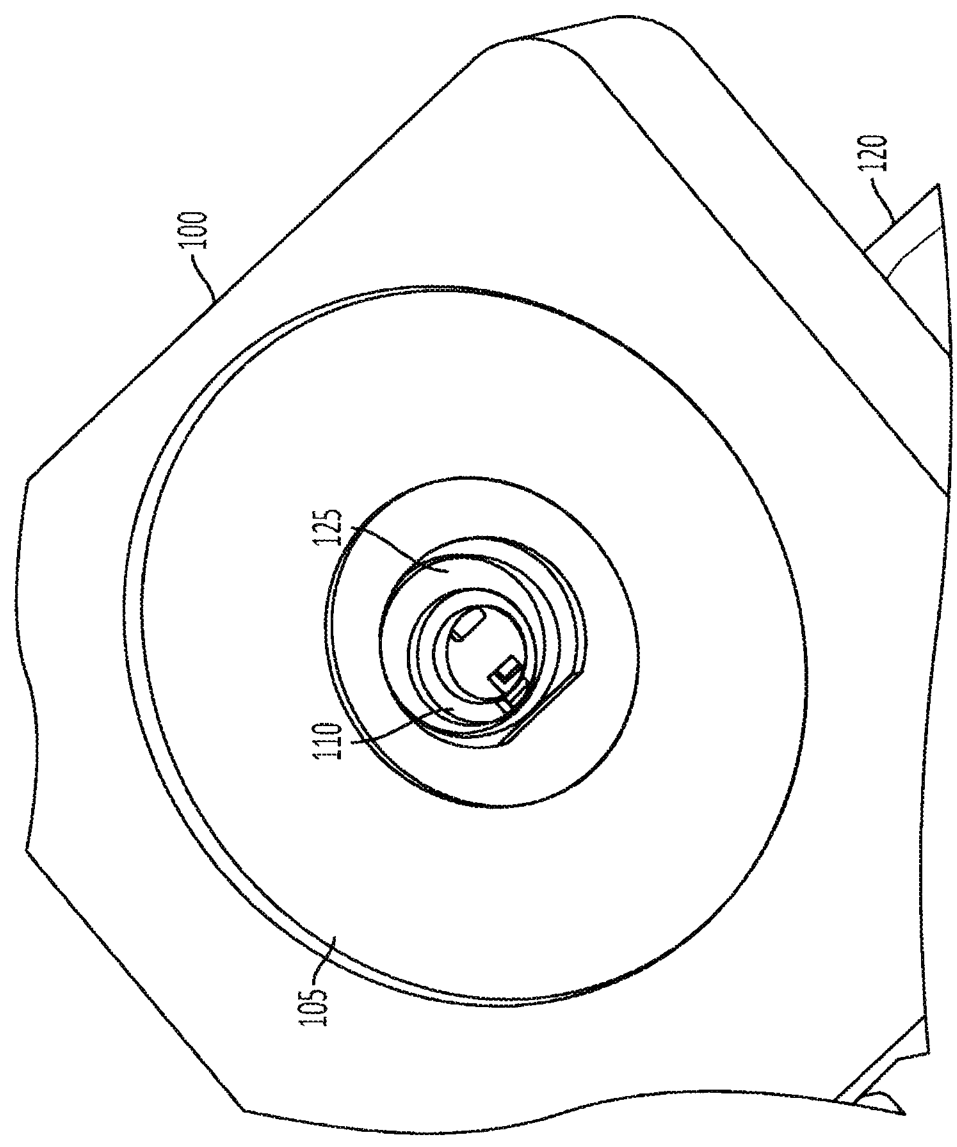
FIG. 4B is a perspective view of a portion of a wearable module, according to an embodiment of the present disclosure.

Light from the output of the wavelength multiplexer 150 illuminates the sample 152. In some embodiments, a speckle mitigation system or coupling optics 160 (which may include the deformable mirror reflector 130 for reducing the spatial coherence of the probe light, and a micro lens 230 (FIGS. 2B and 3C) for producing a beam of the desired shape in the sample 152), may be present between the output of the wavelength multiplexer 150 and the sample 152. After interacting with the sample in the sample 152, the light may be detected by the photodetector 112. In FIG. 1B, the photodetector 112 is illustrated as being on the opposite side of the sample 152 from the source of the probe light for ease of illustration; in some embodiments the photodetector 112 is positioned on the same side of the sample as the source of the probe light, and the probe light may reach the photodetector 112 after scattering one or more times within the sample. This type of optical path may be important for measurements made (e.g., by a spectrophotometer module 100 as illustrated in FIGS. 4A and 4B) by illuminating a first location on the skin of a patient with probe light (transmitted through the transmitting window 105), and detecting light returning from the skin at a second location near the first location (through the receiving window 110).

The photodiode signal may be amplified by a suitable amplifier, and converted to a digital signal by an analog to digital converter, and the resulting digital signal may be fed to the controller 155 for further processing. A power meter 170 and a wavelength meter 175 may measure the optical power and wavelength, respectively, of the probe light, and (i) corrections may be made (e.g., by the controller 155) by adjusting, e.g., the drive currents of the lasers or drive currents of heaters controlling the temperatures of respective gratings of the lasers, or (ii) errors in the transmitted power or wavelength may be compensated for when the data are analyzed. The ratio, as a function of wavelength, of (i) the optical power detected by the photodetector 112 to (ii) the optical power transmitted in the probe light may be referred to herein as a "spectrum".

Estimates of concentrations of biomarkers (e.g., compounds such as glucose, creatinine, urea, lactate, water or alcohol within the tissues of the subject) may be generated, for example, by fitting a measured spectrum with a combination of signatures, each signature being the spectrum that would be expected if a single biomarker were present in the sample at a certain reference concentration.

FIG. 2A shows the structure below the skin contact surface 115, in some embodiments. A support plate 205 (which may be secured to, or part of, the enclosure of the module) includes (e.g., as integral parts) a pedestal 210 for supporting the light source 215, and an angled support 220 for supporting the deformable mirror reflector 130. As shown in FIG. 2B, the deformable mirror reflector 130 may be supported on piezoelectric actuators 225 (e.g., on three piezoelectric actuators 225) that are secured to a base 227 and that operate as support posts. In operation the piezoelectric actuators 225 may be driven by a suitable electric drive signal to vibrate at one or more frequencies between 100 kHz and 1 MHz, e.g., between 400 kHz and 500 kHz. The angled support 220 may be sufficiently rigid to enable the piezoelectric actuators 225 to produce sufficiently large and repeatable motion of the points at which the deformable mirror reflector 130 is supported on the piezoelectric actuators 225. For example, the angled support 220 may be sufficiently rigid to prevent excess energy absorption (or "damping") of the motion produced by the piezoelectric actuators 225.

Figure 2D:
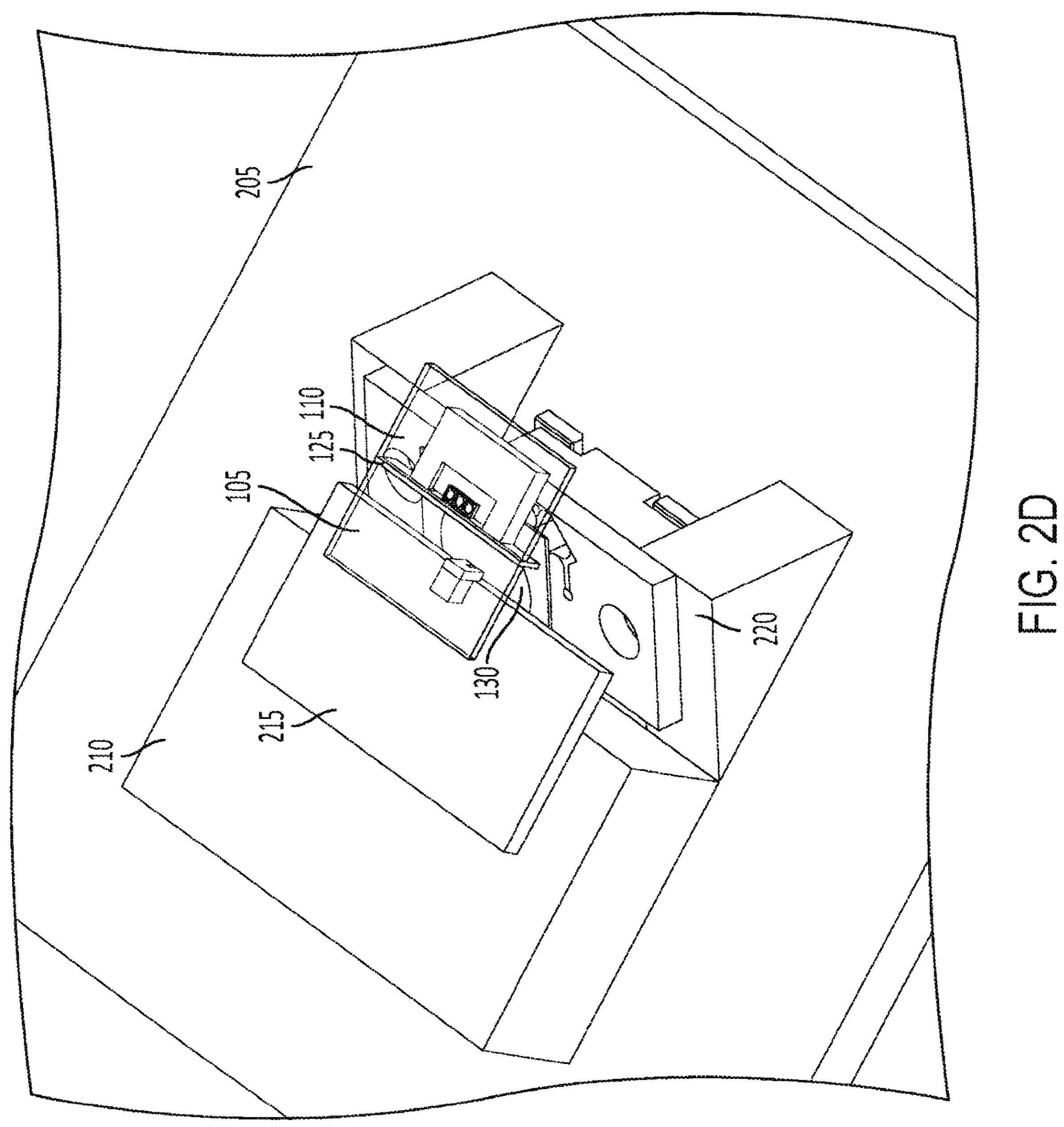
FIG. 2D is a perspective view of a portion of a wearable module, according to an embodiment of the present disclosure.

FIG. 2C is a cross sectional side view of one embodiment. Light exits the light source 215 (which may be a photonic integrated circuit) at a facet (e.g., a waveguide facet of a waveguide that guides light to the edge of the photonic integrated circuit). This facet is at the right edge of the photonic integrated circuit in the view of FIG. 2C. The light exiting the facet propagates through a micro lens 230 secured to the photonic integrated circuit by a support block 235 (which may be secured to both the micro lens 230 and the photonic integrated circuit by a suitable adhesive (e.g., by an epoxy). The micro lens 230 may be a cylindrical lens the shape of which is selected to shape the beam (e.g., to cause horizontal and vertical divergence angles of the beam to be substantially the same), or it may be a spherical lens (FIG. 2B). Angles and dimensions may be as follows: A1: between 45° and 65°, e.g., 55°; A2: between 30° and 45°, e.g., 35°; D1: between 0.1 mm and 0.7 mm, e.g., 0.4 mm; D2: between 0.3 mm and 2 mm, e.g., 1 mm; D3: between 1 mm and 4 mm, e.g., 2.5 mm; D4: between 2 mm and 12 mm, e.g., 7 mm; and D5: between 0.5 mm and 2 mm, e.g., 1 mm. As such, the length of the optical path between the micro lens 230 and the transmitting window 105 may be less than 5 mm. FIG. 2D is a view of an embodiment similar to the embodiment of FIG. 2A, from a different angle.

Figure 2E:
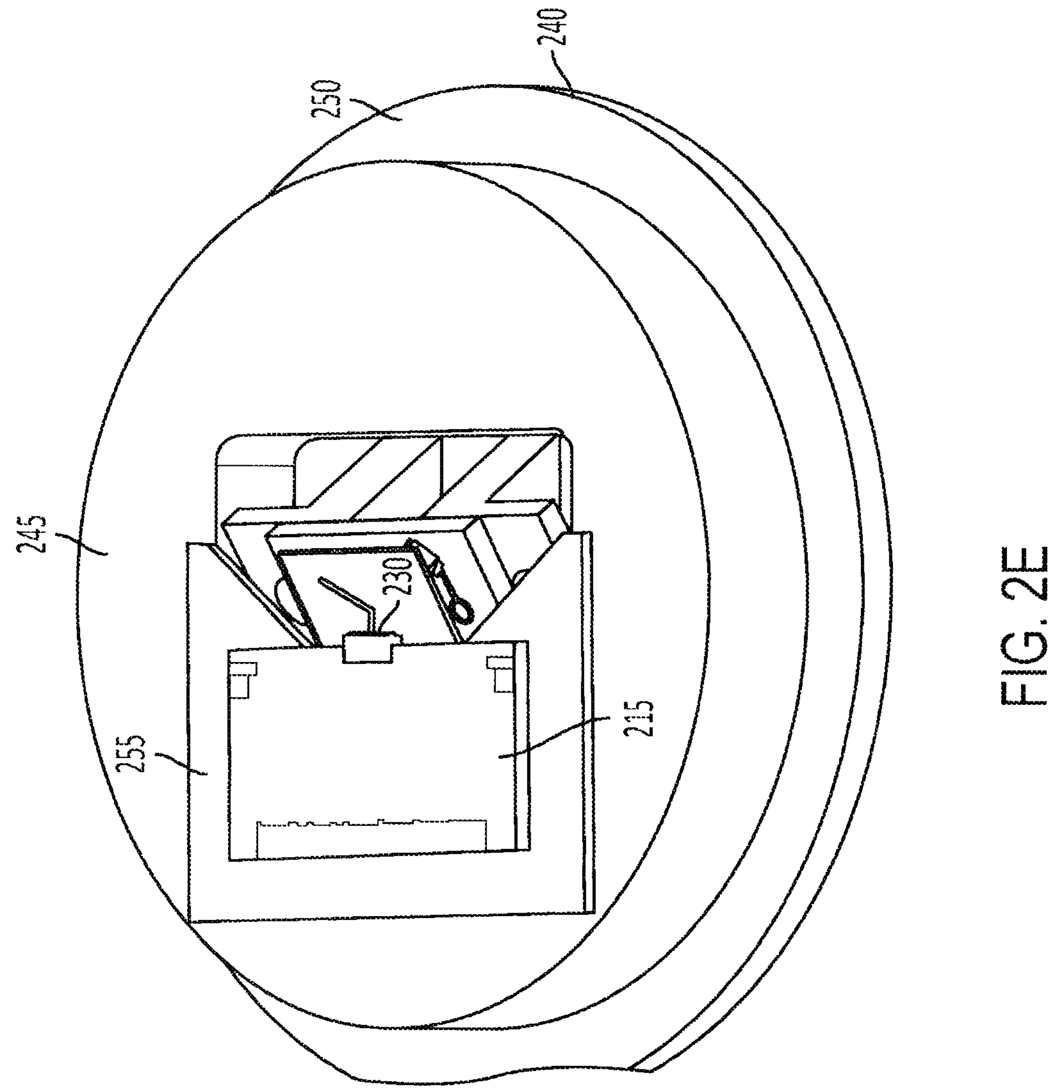
FIG. 2E is a perspective view of a portion of a wearable module, according to an embodiment of the present disclosure.
Figure 2F:
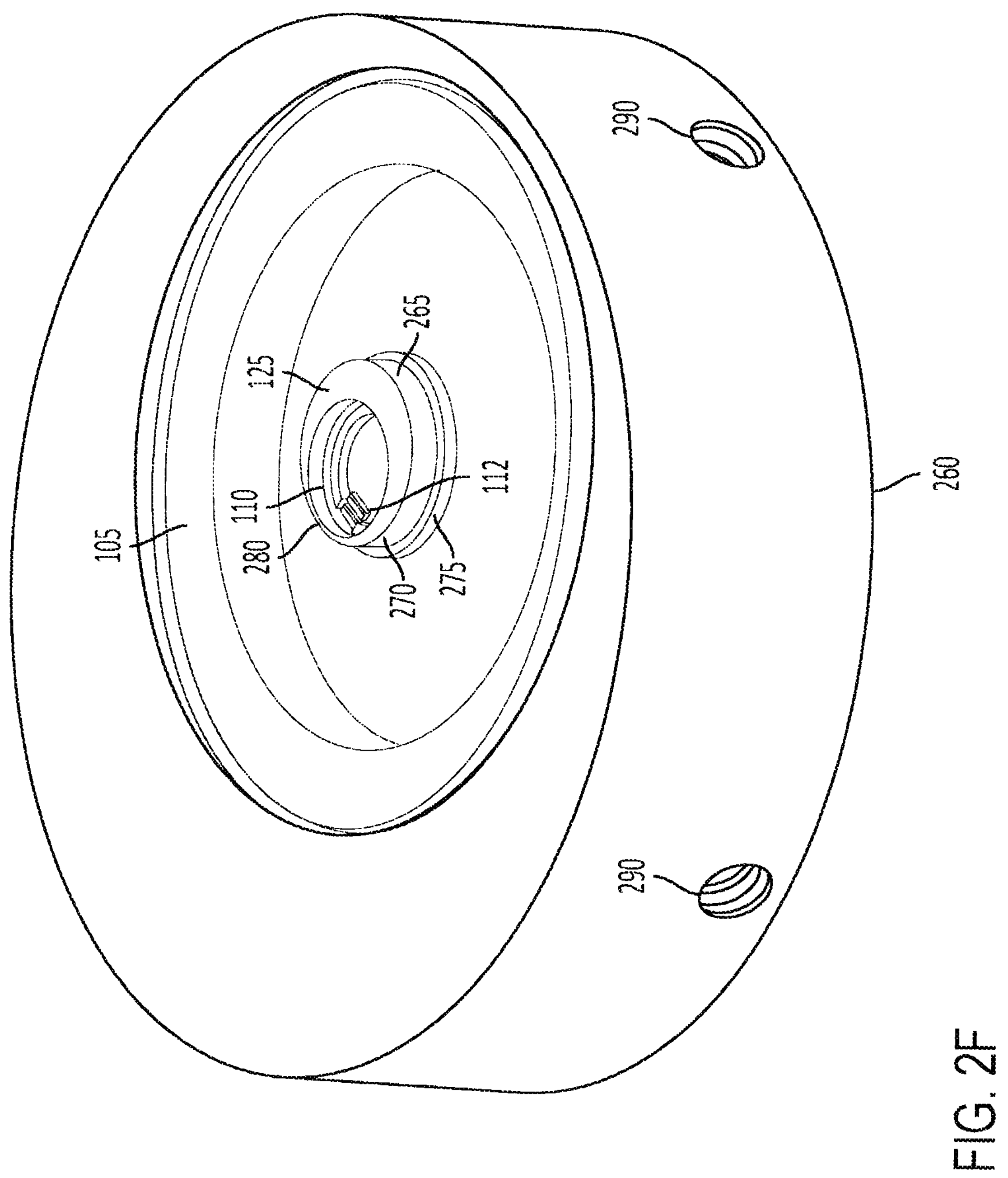
FIG. 2F is a perspective view of a portion of a wearable module, according to an embodiment of the present disclosure.
Figure 2G:
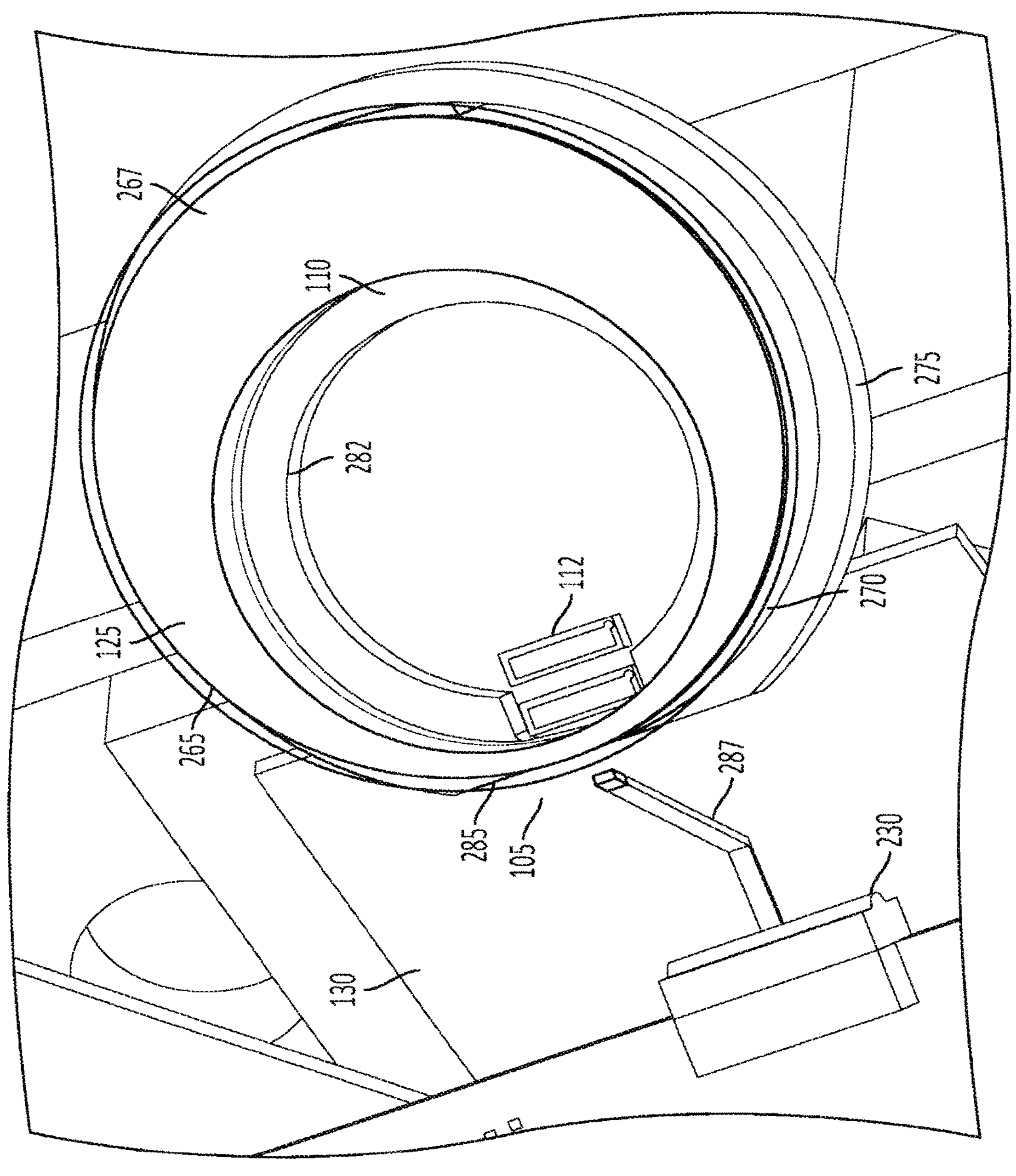
FIG. 2G is a perspective view of a portion of a wearable module, according to an embodiment of the present disclosure.

In some embodiments, the light source 215, the angled support 220, and the deformable mirror reflector 130 are each mounted on or in a round package base 240, as illustrated in FIG. 2E. The package base 240 may include a substantially cylindrical central portion 245 and a flange 250, as shown. The photonic integrated circuit of the light source 215 may be mounted on a sub-mount 255 (e.g., an aluminum nitride sub-mount 255) which may in turn be mounted on the central portion 245. A lid 260, illustrated in FIG. 2F, may fit over the package base 240. The lid 260 includes the transmitting window 105 and the receiving window 110, as well as an enclosure 265 for the photodetector 112 which forms the optically sealed compartment for the photodetector 112, including the opaque barrier 125 between the transmitting window 105 and the receiving window 110. The outer surface of the enclosure 265 for the photodetector 112 may have an upper cylindrical portion 270 and a flange 275 (which may abut against the lower surface of the transmitting window 105 to set the height, relative to the transmitting window 105, of the enclosure 265 for the photodetector 112). The enclosure 265 for the photodetector 112 may have a substantially cylindrical bore forming the compartment containing the photodetector 112. The bore may be offset, as illustrated, from the upper cylindrical portion 270 (e.g., the axis of the bore may be parallel to and offset from the axis of the upper cylindrical portion 270), so that the vertical wall of the enclosure 265 for the photodetector 112 (which forms the opaque barrier 125 between the transmitting window 105 and the receiving window 110) has a non-uniform width, with a thinnest point 280 where the wall of the bore is nearest to the upper cylindrical portion 270.

As in the embodiment of FIG. 1, the gap between the transmitting window 105 and the receiving window 110 at the thinnest point 280 may be made to be small (e.g., between 0.05 mm and 2 mm, or less than 0.3 mm) so that the minimum length through the sample of an optical path extending through the transmitting window 105 and through the receiving window 110 may be relatively short.

FIG. 2G is an enlarged view of the enclosure 265 for the photodetector 112, and of other nearby structures, in some embodiments. The enclosure 265 for the photodetector 112 may include the receiving window 110 and a metal housing 267. The metal housing may be opaque and, as such, the enclosure 265 for the photodetector 112 may be optically sealed except at the receiving window 110. The compartment for the photodetector 112 has a step 282 near the bottom, against which the lower surface of the receiving window 110 may abut, to set the height, relative to the enclosure 265 for the photodetector 112, of the receiving window 110. The step 282 may have a cutout, as shown, to accommodate the photodetector 112. FIG. 2G shows the probe beam 287 exiting the micro lens 230, reflecting from the deformable mirror reflector 130, and propagating toward the transmitting window 105. The flange 275 may have a cutout (e.g., a flat portion) 285 to avoid interfering with the probe beam 287.

Figure 2H:
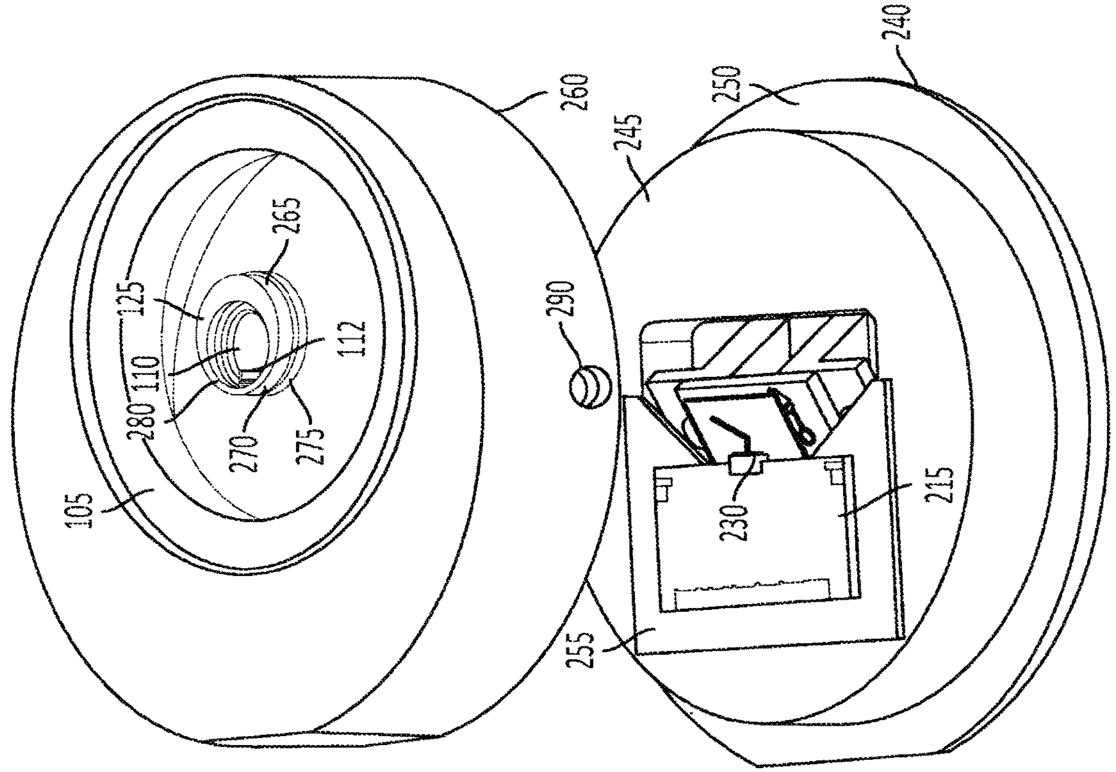
FIG. 2H is a perspective view of a portion of a wearable module, according to an embodiment of the present disclosure.
Figure 2I:
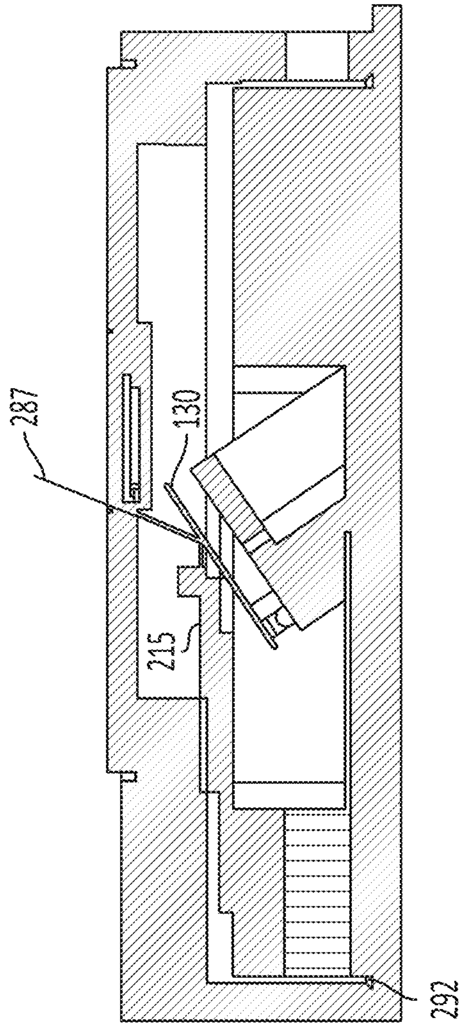
FIG. 2I is a perspective cutaway view of a portion of a wearable module, according to an embodiment of the present disclosure.
Figure 2J:
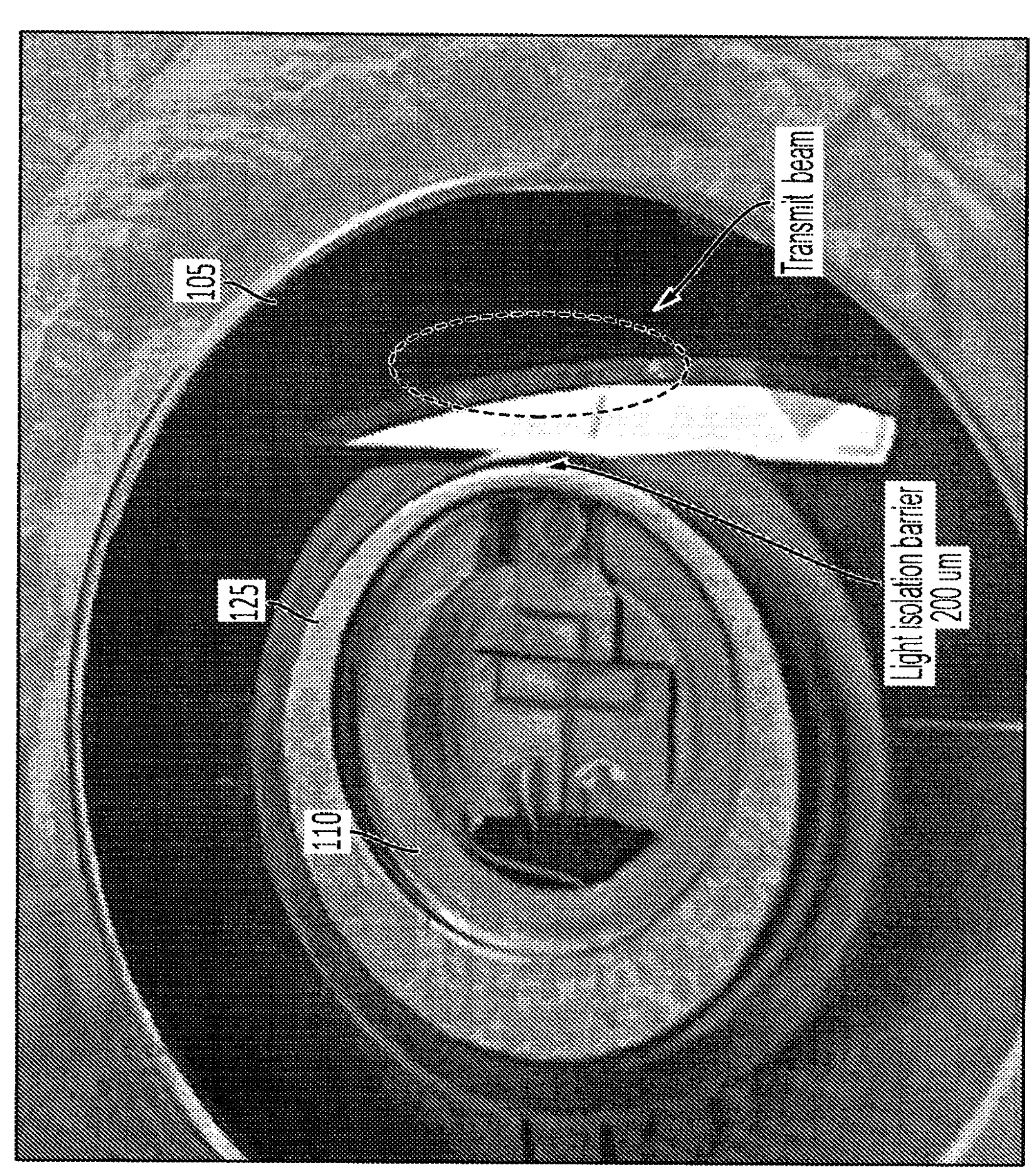
FIG. 2J is a photograph of a reduction to practice, according to an embodiment of the present disclosure.

The lid 260 may fit over the package base 240 as illustrated in FIGS. 2H and 2I. As shown in FIG. 2I, the bottom surface of the lid 260 may abut against the upper surface of the flange 250 of the package base 240, and a small gap 292 between the vertical wall of the lid 260 and the central portion 245 of the package base 240 may allow the position of the lid 260 to be adjusted, relative to the package base 240, in the X and Y directions (two directions parallel to the upper surface of the flange 250 of the package base 240). Screws (e.g., set screws) threaded into threaded holes 290 (FIG. 2F) in the wall of the lid 260 to press against the central portion 245 of the package base 240 may be used to make these adjustments, while monitoring the shape of the probe beam 287, using a beam profiler. By this method, the probe beam 287 may be brought to a position at which it is as close as possible to the opaque barrier 125 without being blocked, to an unacceptable extent, by the opaque barrier 125. This may make it possible to assemble the module 100 in a manner that results in a highly repeatable probe beam location, at the transmitting window 105, relative to the opaque barrier 125 and the photodiode. The probe beam 287 may tilt toward the receiving window 110, as shown in FIG. 2I. In some embodiments, the angle A3 between a line perpendicular to the transmitting window 105 and the direction of the probe beam 287 is between 0 degrees and 30 degrees, e.g., 20 degrees. FIG. 2J is a photograph of a reduction to practice.

Figure 3A:
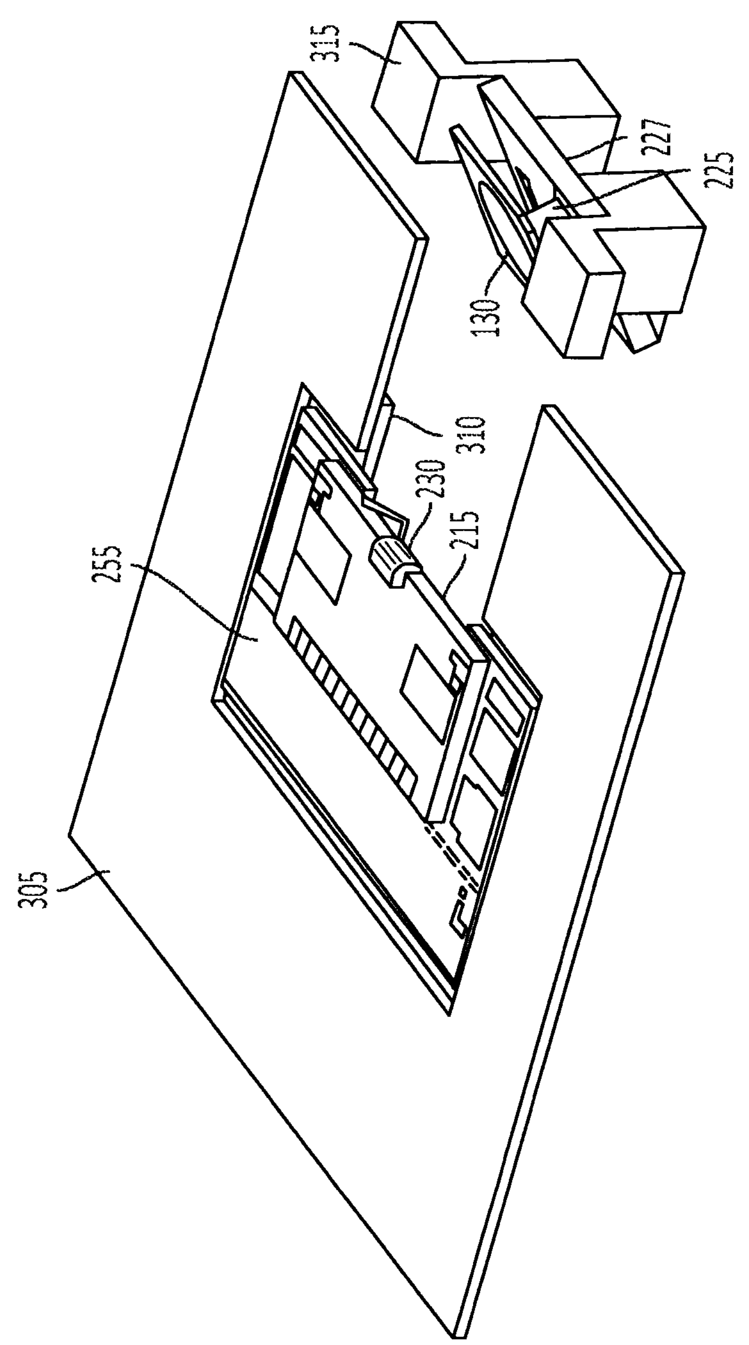
FIG. 3A is a perspective view of a portion of a wearable module, according to an embodiment of the present disclosure.
Figure 3B:
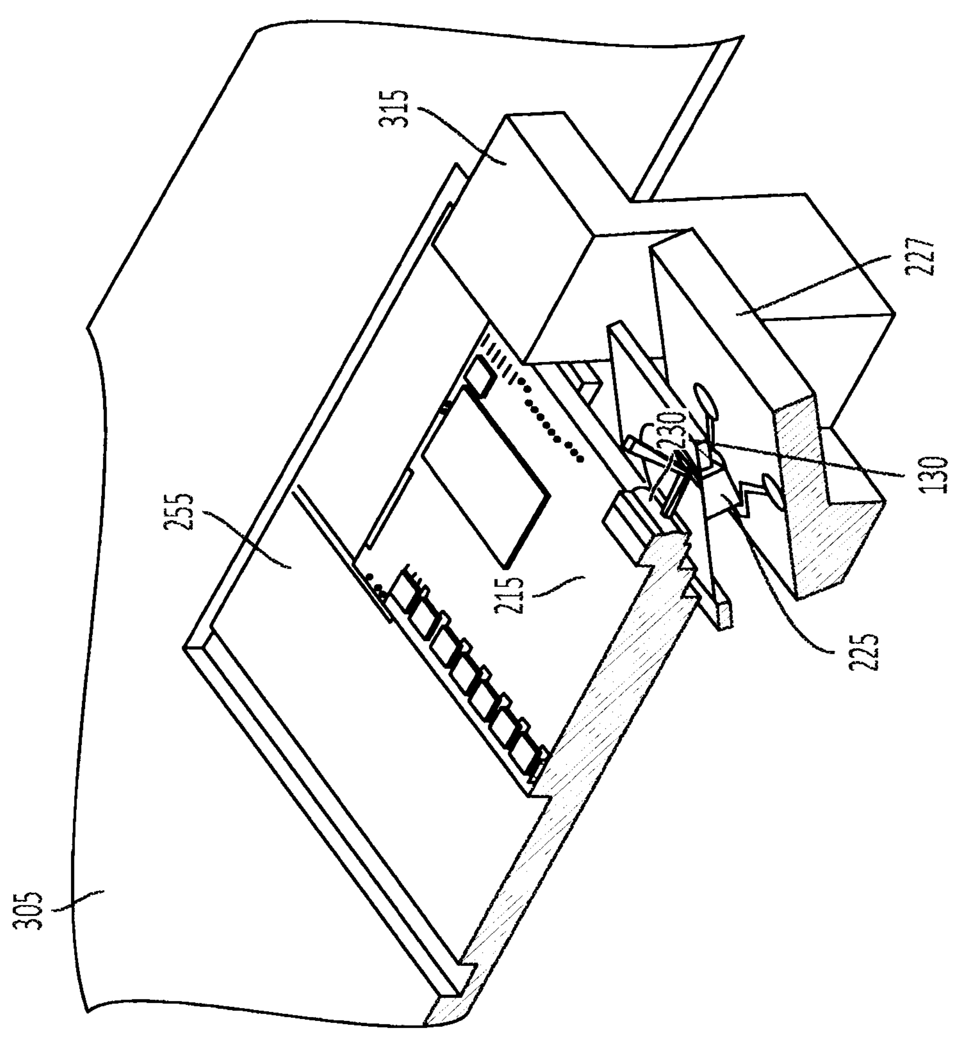
FIG. 3B is a perspective cutaway view of a portion of a wearable module, according to an embodiment of the present disclosure.

FIG. 3A shows an embodiment in which a printed circuit board 305 supports a metal sheet 310 (e.g., a U-shaped metal sheet) which supports an aluminum nitride sub-mount 255, on which is mounted the light source 215. The printed circuit board 305, the metal sheet 310, the aluminum nitride sub-mount 255, and the light source 215 may be secured together by adhesive (e.g., by a suitable epoxy) at the surfaces at which they abut against each other. A T-support 315 supports the base 227 which supports the piezoelectric actuators 225 and the deformable mirror reflector 130. The T-support 315 slides into a gap in the printed circuit board 305; this provides a mechanism for passively aligning the deformable mirror reflector 130 to the light source 215. FIG. 3B shows an enlarged cutaway view of the embodiment of FIG. 3A. FIG. 3C shows an enlarged cutaway view of the embodiment of FIG. 3A with the lid 260 installed.

FIG. 4A shows a module 100 in one embodiment, in which the edges of the transmitting window 105 and the receiving window 110 that are separated by the opaque barrier 125 are substantially straight. The opaque barrier 125 may be a thin strip of metal secured between the transmitting window 105 and the receiving window by adhesive (e.g., by epoxy).

FIG. 4B shows a module 100 in an embodiment in which the receiving window 110 is a round (e.g., circular) window surrounded by the opaque barrier 125 (which has a non-uniform thickness) which is in turn surrounded by the transmitting window 105. The modules of the embodiments of FIGS. 4A and 4B may have ingress protection levels 6 and 7 for solid particles and liquid ingress respectively (IP67). For example, the modules of the embodiments of FIGS. 4A and 4B may be waterproof. As used herein, "waterproof" means capable of being immersed in water up to 1 m deep without ingress of water in harmful quantity.

As used herein, "a portion of" something means "at least some of" the thing, and as such may mean less than all of, or all of, the thing. As such, "a portion of" a thing includes the entire thing as a special case, i.e., the entire thing is an example of a portion of the thing. As used herein, when a second quantity is "within Y" of a first quantity X, it means that the second quantity is at least X−Y and the second quantity is at most X+Y. As used herein, when a second number is "within Y %" of a first number, it means that the second number is at least (1−Y/100) times the first number and the second number is at most (1+Y/100) times the first number. As used herein, the word "or" is inclusive, so that, for example, "A or B" means any one of (i) A, (ii) B, and (iii) A and B.

Each of the terms "processing circuit" and "means for processing" is used herein to mean any combination of hardware, firmware, and software, employed to process data or digital signals. Processing circuit hardware may include, for example, application specific integrated circuits (ASICs), general purpose or special purpose central processing units (CPUs), digital signal processors (DSPs), graphics processing units (GPUs), and programmable logic devices such as field programmable gate arrays (FPGAs). In a processing circuit, as used herein, each function is performed either by hardware configured, i.e., hard-wired, to perform that function, or by more general-purpose hardware, such as a CPU, configured to execute instructions stored in a non-transitory storage medium. A processing circuit may be fabricated on a single printed circuit board (PCB) or distributed over several interconnected PCBs. A processing circuit may contain other processing circuits; for example, a processing circuit may include two processing circuits, an FPGA and a CPU, interconnected on a PCB.

As used herein, when a method (e.g., an adjustment) or a first quantity (e.g., a first variable) is referred to as being "based on" a second quantity (e.g., a second variable) it means that the second quantity is an input to the method or influences the first quantity, e.g., the second quantity may be an input (e.g., the only input, or one of several inputs) to a function that calculates the first quantity, or the first quantity may be equal to the second quantity, or the first quantity may be the same as (e.g., stored at the same location or locations in memory as) the second quantity.

Spatially relative terms, such as "beneath", "below", "lower", "under", "above", "upper" and the like, may be used herein for ease of description to describe one element or feature's relationship to another element(s) or feature(s) as illustrated in the figures. It will be understood that such spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the terms "substantially," "about," and similar terms are used as terms of approximation and not as terms of degree, and are intended to account for the inherent deviations in measured or calculated values that would be recognized by those of ordinary skill in the art.

It will be understood that when an element or layer is referred to as being "on", "connected to", "coupled to", or "adjacent to" another element or layer, it may be directly on, connected to, coupled to, or adjacent to the other element or layer, or one or more intervening elements or layers may be present. In contrast, when an element or layer is referred to as being "directly on", "directly connected to", "directly coupled to", or "immediately adjacent to" another element or layer, there are no intervening elements or layers present.

Any numerical range recited herein is intended to include all sub-ranges of the same numerical precision subsumed within the recited range. For example, a range of "1.0 to 10.0" or "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Similarly, a range described as "within 35% of 10" is intended to include all subranges between (and including) the recited minimum value of 6.5 (i.e., (1−35/100) times 10) and the recited maximum value of 13.5 (i.e., (1+35/100) times 10), that is, having a minimum value equal to or greater than 6.5 and a maximum value equal to or less than 13.5, such as, for example, 7.4 to 10.6. Any maximum numerical limitation recited herein is intended to include all lower numerical limitations subsumed therein and any minimum numerical limitation recited in this specification is intended to include all higher numerical limitations subsumed therein.

Although exemplary embodiments of a wearable module including a spectrophotometer have been specifically described and illustrated herein, many modifications and variations will be apparent to those skilled in the art. Accordingly, it is to be understood that a wearable module including a spectrophotometer constructed according to principles of this disclosure may be embodied other than as specifically described herein. The invention is also defined in the following claims, and equivalents thereof.

What is claimed is:

1. A system, comprising:
- a wearable device configured to be worn against a skin of a subject, comprising:
  - a transmitting window;
  - a light source for generating light for transmission through the transmitting window;
  - a receiving window;
  - a photodetector configured to detect the light received through the receiving window; and
  - an opaque barrier,
  - an edge of the transmitting window being separated from an edge of the receiving window by a first gap having a width of less than 2 millimeters (mm), and
  - the opaque barrier being in the first gap,
- wherein the system comprises:
  - a package base comprising the light source; and
  - a lid,
  - the lid comprising:
    - the transmitting window;
    - the receiving window, and
    - the photodetector,
- wherein a lower surface of the lid abuts against an upper surface of a flange of the package base, and a second gap between the lid and the package base enables the lid to slide, on the upper surface of the flange, in a direction parallel to the upper surface of the flange, and
- wherein the lid comprises a threaded hole for receiving a threaded part, the threaded part being configured, when turned, to cause the lid to slide on the upper surface of the flange,
- wherein the opaque barrier is opaque to the light at a wavelength in a range from 2000 nanometers (nm) to 2500 nm,
- wherein the receiving window is:
  - parallel, to within 5 degrees, to the transmitting window;
  - coplanar, at the first gap, to within 0.5 mm, with the transmitting window; and
  - cylindrical and has a cylindrical outer surface,
- wherein the transmitting window has a circular hole, having a larger diameter than the receiving window,
- wherein the opaque barrier has a cylindrical outer surface fitting against an inner surface of the circular hole, and a bore having a cylindrical inner surface fitting against the cylindrical outer surface of the receiving window,
- wherein an axis of the cylindrical inner surface of the bore is parallel to, and offset from, an axis of the cylindrical outer surface of the opaque barrier to define a non-uniform thickness of the opaque barrier,
- wherein at a thinnest point, the non-unform thickness of the opaque barrier is less than 1 mm, and
- wherein the system further comprises a reflector for reflecting light from the light source through the transmitting window.

2. The system of claim 1, wherein at the thinnest point, the opaque barrier has a thickness of less than 0.5 mm.

3. The system of claim 1, comprising a photodetector enclosure comprising the receiving window and the opaque barrier, wherein:
- the photodetector enclosure comprises a step at an end of the bore, and
- a lower surface of the receiving window abuts against the step.

4. The system of claim 3, wherein:
- the photodetector enclosure further comprises a flange, and
- a lower surface of the transmitting window abuts against an upper surface of the flange.

5. The system of claim 1, wherein the reflector is a deformable reflector.

6. The system of claim 5, further comprising a piezoelectric actuator configured, when driven by an electric drive signal, to cause the deformable reflector to deform.

7. The system of claim 1, wherein the light source comprises:
- a photonic integrated circuit, comprising a waveguide having an output facet at an edge of the photonic integrated circuit; and
- a lens, secured to the edge of the photonic integrated circuit.

8. The system of claim 1, wherein the wearable device is waterproof.

* * * * *